United States Patent [19]

Frantz

[11] Patent Number: 4,930,171

[45] Date of Patent: Jun. 5, 1990

[54] CONTOUR RETAINING SUPPORT CUSHION

[75] Inventor: Ronald F. Frantz, Barrington, Ill.

[73] Assignee: International Healthcare Products, Inc., Northbrook, Ill.

[21] Appl. No.: 347,170

[22] Filed: May 3, 1989

[51] Int. Cl.$^5$ .......................... A47C 27/18; A47C 1/00
[52] U.S. Cl. .......................................... 5/450; 5/451; 5/464; 5/432; 297/DIG. 1
[58] Field of Search .................. 5/450, 451, 449, 481, 5/464, 448, 441, 454; 297/DIG. 1, DIG. 3

[56] References Cited

U.S. PATENT DOCUMENTS

| | | |
|---|---|---|
| 2,412,112 | 12/1946 | Wood et al. . |
| 2,855,986 | 10/1958 | Engelen, Sr. . |
| 3,177,036 | 4/1965 | Halter . |
| 3,192,099 | 6/1965 | Beckman et al. . |
| 3,192,540 | 7/1965 | Swank . |
| 3,253,861 | 5/1966 | Howard . |
| 3,308,491 | 3/1967 | Spence . |
| 3,463,547 | 8/1969 | Brennan et al. . |
| 3,503,649 | 3/1970 | Johnson . |
| 3,605,145 | 9/1971 | Graebe . |
| 3,616,471 | 11/1971 | Braun ........................ 5/450 |
| 3,663,973 | 5/1972 | Spence . |
| 3,689,948 | 9/1972 | Graves et al. . |
| 3,689,949 | 9/1972 | Weinstein et al. ........................ 5/450 |
| 3,702,484 | 11/1972 | Tobinick et aL. ........................ 5/450 |
| 3,721,232 | 3/1973 | Trenchard . |
| 3,787,908 | 1/1974 | Beck et al. . |
| 3,815,165 | 6/1974 | Tobinick et al. ........................ 5/450 |
| 3,848,282 | 11/1974 | Viesturs ........................ 5/457 |
| 3,858,379 | 1/1975 | Graves et al. . |
| 3,864,766 | 2/1975 | Prete, Jr. ........................ 5/450 |
| 3,870,450 | 3/1975 | Graebe ........................ 425/269 |
| 3,872,525 | 3/1975 | Lea et al. ........................ 5/450 |
| 3,935,690 | 2/1976 | Lea et al. . |
| 4,025,974 | 5/1977 | Lea et al. . |
| 4,038,762 | 8/1977 | Swan, Jr. . |
| 4,073,021 | 2/1978 | Carlisle . |
| 4,083,127 | 4/1978 | Hanson ........................ 36/93 |
| 4,132,228 | 1/1979 | Green . |
| 4,144,658 | 3/1979 | Swan, Jr. ........................ 36/71 |
| 4,190,697 | 2/1980 | Ahrens ........................ 297/DIG. 1 |
| 4,312,087 | 1/1982 | De Geus ........................ 5/490 |
| 4,370,768 | 2/1983 | Saloff ........................ 5/450 |
| 4,370,769 | 2/1983 | Herzig et al. ........................ 5/441 |
| 4,382,306 | 5/1983 | Lickert ........................ 5/441 |
| 4,541,136 | 9/1985 | Graebe ........................ 5/455 |
| 4,588,229 | 5/1986 | Jay ........................ 5/450 |
| 4,624,877 | 11/1986 | Lea et al. . |
| 4,643,481 | 2/1987 | Saloff et al. .................. 297/DIG. 1 |
| 4,672,700 | 6/1987 | Poncy ........................ 5/450 |
| 4,698,864 | 10/1987 | Graebe ........................ 5/441 |
| 4,713,854 | 12/1987 | Graebe ........................ 297/DIG. 1 |
| 4,726,624 | 2/1988 | Jay ........................ 5/450 |
| 4,730,610 | 3/1988 | Graebe . |

FOREIGN PATENT DOCUMENTS

| | | |
|---|---|---|
| 918227 | 9/1954 | Fed. Rep. of Germany . |
| 302008 | 12/1928 | United Kingdom . |
| 439936 | 12/1935 | United Kingdom . |
| 978348 | 12/1964 | United Kingdom . |
| 1302522 | 1/1973 | United Kingdom . |
| 2026315 | 2/1980 | United Kingdom . |
| 2074034 | 10/1981 | United Kingdom . |
| 2082907 | 3/1982 | United Kingdom . |

OTHER PUBLICATIONS

Sheet CP4 Carbopol High Performance Polymers For Pharmaceuticals, Official Monograph of Carbomer

(List continued on next page.)

Primary Examiner—Alexander Grosz
Attorney, Agent, or Firm—Dressler, Goldsmith, Shore, Sutker & Milnamow, Ltd.

[57] ABSTRACT

A support cushion has a flexible, airtight casing having a support layer on one side defining a support surface for being engaged by a portion of a body to be supported. A resilient layer of foam is disposed within the casing generally coextensive with the casing support layer support surface for normally urging the casing toward an expanded condition. A fluid-filled pad is positioned within the casing adjacent the additional foam material. A valve is mounted to the casing for communicating with the interior of the casing and is operable for preventing or permitting flow of air through the valve into and out of the casing.

33 Claims, 2 Drawing Sheets

OTHER PUBLICATIONS

934P, *USP National Formulary*, (vol. XVI, 1985 Edition), The B. F. Goodrich Co.

Sheet CP1 Carbopol High Performance Polymers, Material Data Sheet, issued Nov., 1987, B. F. Goodrich Co.

Zero-G Weight Distribution System, Steridyne Corporation, 1984.

Gel-Foam Pad, advertisement sheet (Skil-Care).

The Roho Tri-Max Seating System, advertisement sheet Roho, Inc.

Akros ZP Wheelchair Seating System, by Lumex.

Jobst Hydro-Float, by Jobst.

Contour Flotation Cushion Elasto-Gel Contour Flotation Cushion.

T-Foam AliMed Cushion, *Paraplegia News*, Feb. 1988.

Gaymar Sof. Care Chair Cushion, Gaymar Industries, Inc., 3/15/87.

Lotus WC1517 Water Flotation Cushion for Wheelchair, Lotus Health Care Products advertising sheet.

Lotus PXM3666 with "Flow-Gel" Filling, Lotus Health Care Products advertising sheet.

Lotus SA3280 for Decubitus and Tissue Trauma Care, Lotus Health Care Products advertising sheet.

Lotus DU 3572 AS and DU 3572 DU-care Static Air Flotation Mattress, Lotus Health Care Products advertising sheet.

Lotus MD3677 with "Flow-Gel", Lotus Health Care Products advertising sheet.

Lotus HMX3666 Water Flotation Mattress, Lotus Health Care Products advertising sheet.

Lotus CMGL 2542 with "Flow-Gel", Lotus Health Care Products advertising sheet.

Lotus BT2772 Collapsible Bed-Tub, Lotus Health Care Products advertising sheet.

Experimental Evaluation of Wheelchair Cushions: A Report of a Pilot Study, by George Van B. Cochran, M.D., Med. Sc.D., and Glen Slater, B.S., R.P.T., *Bulletin of Prosthetics Research*, fall 1973.

Wheelchairs for Paraplegic Patients, by A. Bennett Wilson, Jr., *Clinical Prosthetics and Orthotics*, vol. 11, No. 2, pp. 82-90, 1987.

Seating for Children and Young Adults with Cerebral Palsy, by J. Martin Carlson, M.S., C.P.O. et al., *Clinical Prosthetics and Orthotics*, vol. 11, No. 3, pp. 76-198, 1987.

Fluid Support in the Prevention and Treatment of Decubitus Ulders, by James D. Weinstein, M.D. et al., *American Journal of Physical Medicine*, 1966.

Evaluation of Seat Devices Designed to Prevent Ischemic Ulcers in Paraplegic Patients, by Rollin J. Houle, M.D., *Archives of Physical Medicine & Rehabilitation*, Oct., 1969.

Wheelchair Cushions Designed to Prevent Pressure Sores: An Evaluation, Barbara J. DeLateur, M.D. et al., *Archives of Physical Medicine & Rehabilitation*, Mar. 1976.

Comparison of Pressure Distribution Qualities in Seat Cushions, Vert Mooney, M.D. et al., *Bulletin of Prosthetics Research*, spring 1971.

Development of Test Methods for Evaluation of Wheelchair Cushions, by George Van B. Cochran, M.D. et al., *Bulletin of Prosthetics Research*, spring 1980.

A Comparison of Sitting Pressures on Wheelchair Cushions as Measured by Air Cell Transducers and Miniature Electronic Transducers, by V. R. Palmiere, *Bulletin of Prosthetics Research*, spring 1980.

Experimental Evaluation of Wheelchair Cushions, by Geo. Van B. Cochran, M.D. et al., *Bulletin of Prosthetics Research*.

Modular Seat-Shells and Standardized Manufacture of Individually Shaped Seats for the Severely Disabled-The Tubingen Experience, by George Neff et al., Clinical Prosthetics and Orthotics, vol. 11, No. 1, 1987.

Wheelchair Cushions to Reduce Pressure under Bony Prominences, by Sherman G. Sother M.D. et al., Arch. Phys., Med. Rehabil., vol. 55, Oct. 1974.

A Classification of Wheelchair Seating, by Susan Lipton Garber, OTR, *The American Journal of Occupational Therapy*.

Wheelchair Cushions: A Historical Review, Susan Lipton Garber, OTR, *The American Journal of Occupational Therapy*, Jul. 1985.

CONTOUR RETAINING SUPPORT CUSHION

TECHNICAL FIELD

This invention relates to a support cushion for supporting a body or portion of a body. The invention is particularly adapted for use with the human body as a seat cushion, as a back support cushion, or as part of a splint assembly for cushioning or immobilizing a portion of a body.

BACKGROUND OF THE INVENTION AND TECHNICAL PROBLEMS POSED BY THE PRIOR ART

Various types of conventional support cushions have been introduced or proposed for providing a reduced pressure on the body and/or for providing a desired pressure distribution.

Such cushions are typically intended for use by partially or completely immobilized patients who maintain a substantially stationary position for long periods of time. Cushions have been specifically designed for use as seating cushion or back support cushion for a patient when seated in a chair, especially a wheelchair. A variety of these designs are in use or have been proposed which are intended to overcome some of the problems encountered by the patient.

For example, when a person is sitting on a cushion, the person's weight is concentrated to a great extent in the buttock area, and the pressure tends to be greatest in the ischial, trochanter and sacral areas. Excessive pressure on these areas for prolonged periods of time can result in restricted circulation of blood and in tissue necrosis with the resultant formation of pressure sores or decubitis ulcers.

Another problem that must be addressed by an effective cushion design is the stability of the body when placed on or against the cushion. This is especially important with a seat cushion. To the extent that a patient may tilt, lean, or otherwise actually shift position on the cushion, there is a danger that the response of the cushion may be inconsistent with the maintenance of the desired stability. For example, a cushion containing a fluid may not provide sufficient resilience or resistance to movement.

Some cushions contain relatively large amounts of liquid, and this can make the cushion relatively heavy and difficult to handle, especially for elderly, infirm, or disabled persons.

With almost any cushion design, cost considerations are important. A cushion having a complex design may be difficult to manufacture, and may therefore be too costly to be of practical use.

In view of the above-discussed problems, it would be desirable to provide a cushion with improved features and support characteristics and which could still be relatively inexpensively manufactured.

It would be beneficial if such an improved cushion would provide sufficiently low pressures on the body so that the body could be comfortably supported by the cushion with a minimal, or at least reduced, tendency to cause tissue stress and resultant pressure sores.

It would be advantageous if such an improved cushion could be used in a way that would permit the cushion to readily and effectively conform substantially to the contour of the body portion engaged with the cushion.

In addition, it would be desirable to provide an improved cushion which could support a body or portion thereof in a relatively stable manner while still being capable of accommodating the movement or repositioning of the body.

It would also be beneficial if the design of the improved cushion could accommodate fabrication from relatively light weight components so that the overall weight of the cushion is not excessive.

SUMMARY OF THE INVENTION

According to the broad principles of one aspect of the present invention, a support cushion is provided with a flexible, airtight casing. A valve means is mounted to the casing for communicating with the interior of the casing and is operable for preventing or permitting the flow of air through the valve means into and out of the casing.

The cushion further includes a resilient contour-conforming means disposed in the casing for normally urging the casing toward an expanded condition. According to a preferred embodiment embodying the principles of one aspect of the invention, the resilient contour-conforming means is not bonded to the casing.

According to the further principles of the present invention, a novel method is provided for using the cushion. A body can be positioned against the casing with the valve means opened to accommodate the expelling of air from the casing and the conforming of the cushion to the body. The valve means can thereafter be closed to generally maintain the conformance.

According to the broad principles of another aspect of the present invention, the cushion may include a flexible, airtight casing having at least a support layer on one side for being engaged by a portion of the body to be supported. A resilient means is provided in the casing and is generally coextensive with the casing support layer for normally urging the casing toward an expanded condition. The resilient means may be a resilient foam material that may or may not be glued or otherwise attached to the inside of the casing.

A mass of resilient foam material is provided adjacent a portion of the resilient means. The mass of resilient foam material may be of the same material as the resilient means, and indeed, may be a unitary part of the resilient means. Alternatively, the mass of resilient foam material may be a separate material that may or may not be glued or otherwise attached to the resilient means.

A fluid-filled pad is positioned within the casing adjacent another portion of the resilient means.

A valve means is mounted to the casing for communicating with the interior of the casing and is operable for preventing or permitting flow of air through the valve means into and out of the casing. Thus, a body can be positioned against the casing with the valve means opened to accommodate expelling of air from the casing and the conforming of the cuhion to the body. The valve means can thereafter be closed to generally maintain the conformance.

In a preferred form of the cushion of the present invention, the fluid-filled pad is a liquid-filled pad which is configured to provide support for certain portions of the body and not for other portions. Similarly, the mass of resilient foam material adjacent the liquid-filled pad is also configured to provide a particular supporting contour for a portion or portions of the body.

Further, a top layer of resilient foam material preferably covers the liquid-filled pad and the adjacent mass of resilient foam material beneath the casing.

The novel support cushion of the present invention can be configured to provide a relatively stable, low-pressure support for various body portions. The seat cushion can be fabricated relatively inexpensively and without excessive weight.

Further, the support cushion of the present invention accommodates the use of an internal pad filled with fluid, including a liquid that may range from a very low viscosity, pourable liquid to a highly viscous or shape-retaining liquid. This facilitates the conformance of the seat cushion to certain body portion contours. Additionally, the overall contour shape of the cushion can be changed in conformance with the contacting body portion and can be generally maintained in such conformance by the proper use of the cushion valve means for accommodating the introduction, removal, or retention of air or other gas in the airtight casing of the cushion.

Numerous other advantages and features of the present invention will become readily apparent from the following detailed description of the invention, from the claims, and from the accompanying drawings.

BRIEF DESCRIPTION OF THE DRAWINGS

In the accompanying drawings forming part of the specification, in which like numerals are employed to designate like parts throughout the same.

DESCRIPTION OF THE PREFERRED EMBODIMENTS

While this invention is susceptible of embodiment in many different forms, this specification and the accompanying drawings disclose only some specific forms as examples of the use of the invention. The invention is not intended to be limited to the embodiments so described, and the scope of the invention will be pointed out in the appended claims.

The article of this invention has certain structural details and mechanical elements that will be recognized by one skilled in the art. However, the detailed descriptions of such elements are not necessary to an understanding of the invention, and accordingly, are not herein presented.

Figures 1, 2, 3, 5, 6:
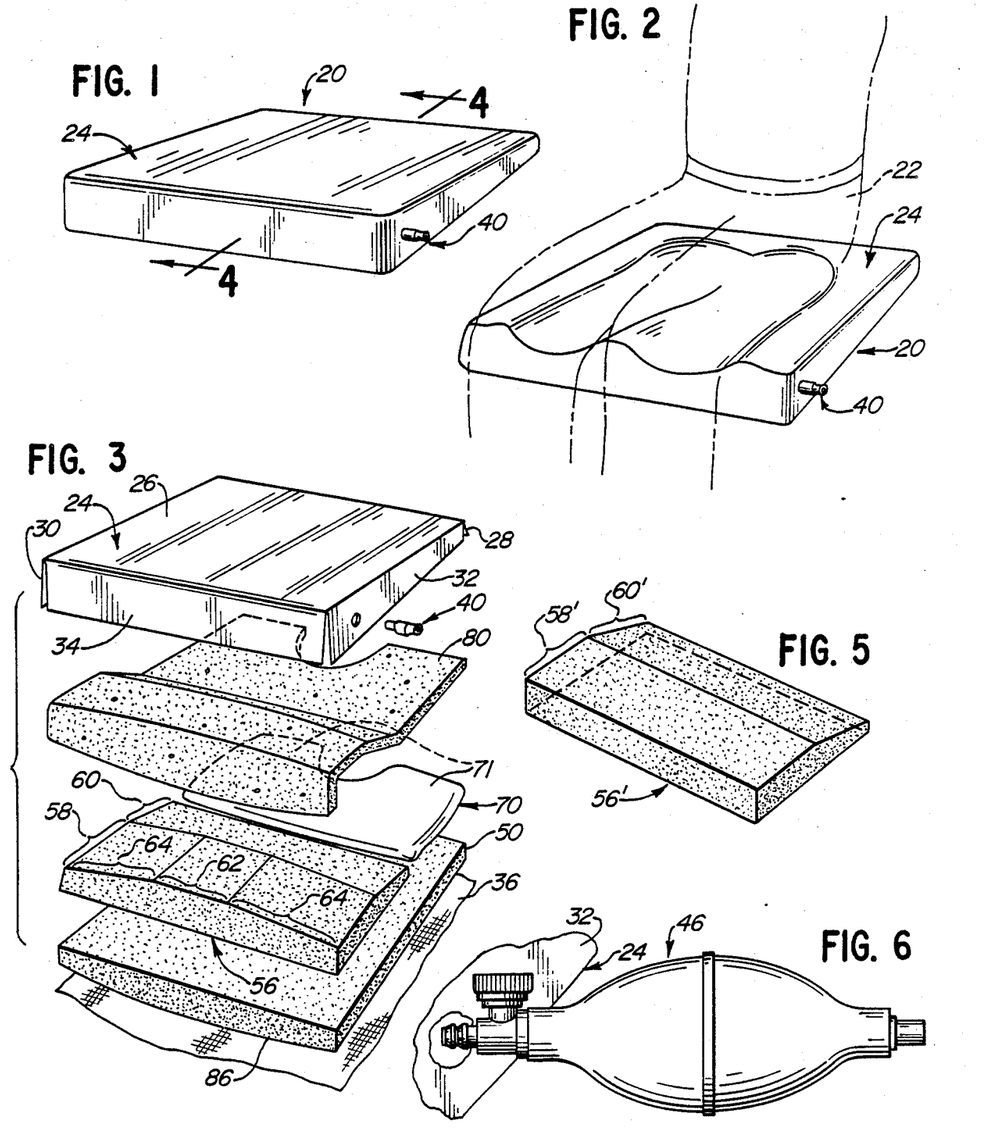
FIG. 1 is a perspective view of a preferred embodiment of a cushion of the present invention adapted for use as a seat cushion.
FIG. 2 is a view similar to FIG. 1 but showing how the cushion conforms to a seated person illustrated in phantom by dashed lines.
FIG. 3 is an exploded, perspective view of the cushion.
FIG. 5 is a perspective view of an alternate embodiment of one of the foam material components of the cushion.
FIG. 6 is a greatly enlarged, fragmentary, perspective view of an alternate embodiment of the valve mechanism with a portion of the casing broken away to better illustrate the valve mechanism.

Referring now to the drawings, a first embodiment of the cushion of the present invention is designated generally by reference numeral 20 in FIG. 1. The cushion 20 is specifically configured for use as a seat cushion for supporting a seated person 22 as illustrated in FIG. 2.

The cushion 20 includes a flexible, airtight cover or casing 24. As best illustrated in FIG. 3, the casing 24 includes an upper or top sheet 26 which functions as a top support layer defining a support surface for being contacted by the portion of the body 22 under which the cushion 20 is disposed. The top support layer sheet 26 includes a rear flap 28, a left side flap 30, a right side flap 32, and a front flap 34. The casing 24 further includes a bottom sheet 36 functioning as a bottom bearing layer. The exterior surface of the sheet 36 typically rests on a chair, wheelchair seat, bed, or the like.

In the preferred embodiment illustrated, the cover or casing 24 is fabricated from a durable, flexible, elastomeric material The casing's top sheet 26 and bottom sheet 36 are sealed together around the cushion internal components (described hereinafter in detail). The front flap 34 is sealed to the left and right side flaps 30 and 32 at the cushion corners in the front. The rear flap 28 is sealed to the left and right side flaps 30 and 32 at the cushion corners in the back. The bottom margins of the flaps 28, 30, 32, and 34 are sealed to the periphery of the bottom layer sheet 36. The sealing may be effected with glue, by vulcanizing, or by radio frequency welding.

The casing 24 may be fabricated from a variety of conventional materials, for example, from a five ounce per square yard polyurethane-coated nylon twill material sold under the trade name "Uretek" in the United States of America by Uretek, Inc., 30 Lenox Street, New Haven, Connecticut 06513, U.S.A., or sold under the trade name "Lamotec" in the United States of America by Lamotec, Inc., 1 Mountain Road, Burlington, Maine 01803, U.S.A.

A valve means or valve 40 is mounted to the cover or casing 24 for communicating with the interior of the casing 24. The valve 40 is operable between open and closed positions. In the open position the valve 40 permits flow of air or other gases through the valve 40 into the casing and out of the casing. The valve 40 can be closed for preventing the flow of the air or other gas through the valve into and out of the casing. One conventional valve that may be used is the insertion valve sold under the designation #160-AC in the United States of America by Halkey-Roberts, 11600 Ninth Street, N., St. Petersburg, Florida 33702 U.S.A.

In a modification illustrated in FIG. 6, the valve may be incorporated in a conventional valve/pump assembly 46 for effecting positive inflation of the casing 24. The valve/pump assembly 46 can be closed after a desired amount of air has been pumped into the casing 24. On the other hand, the valve/pump assembly 46 can be opened to permit the air to be expelled from the casing 24 when desired.

The suitable hand inflation valve/pump assembly 46 that may be used is that which is sold in the United States of America under the generic description "hand pump assembly" and trade designation CVI15700 by Halkey-Roberts, 11600 Ninth Street, N., St. Petersburg, Florida 33702, U.S.A.

Figure 4:
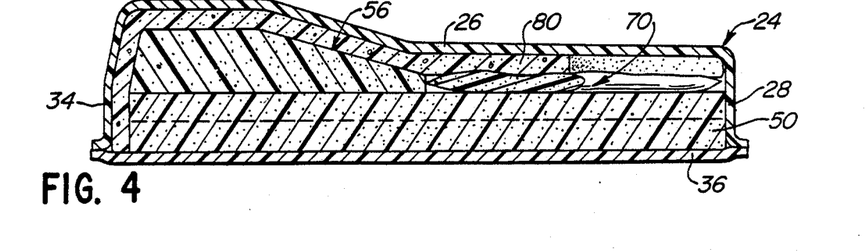
FIG. 4 is a greatly enlarged, cross-sectional view taken generally along the plane 4—4 in FIG. 1.

A resilient contour-conforming means is disposed within the casing 24 as best illustrated in FIGS. 3 and 4. In the preferred embodiment illustrated, the resilient contour-conforming means includes a bottom layer of foam material 50, an additional mass of foam material 56, and a top layer of foam material 80.

The foam material 50 is generally coextensive with the support surface of the casing support layer sheet 26 on one side of the cushion 20 and with the casing bottom bearing layer 36 on the other side of the cushion 20. The resilient foam materials 50, 56, and 80 normally urge the casing 24 toward an expanded condition, and the cushion 20 thus assumes its expanded condition when the valve means 40 is open and the cushion 20 is not under load as illustrated in FIG. 1.

If the cushion 20 is intended for use in a wheelchair, then the bottom layer of resilient foam material 50 is preferably provided with a downwardly convex lower surface 86 (FIG. 3) so as to generally conform with a curvature of a conventional wheelchair sling seat.

The resilient bottom layer of foam material 50, in the preferred embodiment illustrated, is an open cell, high density, polyurethane foam having an indentation load deflection from between about 35 to 45 pounds per square inch area at 25 per cent indentation. As used herein, the term "indentation load deflection" is defined as the measurement of the load necessary to produce a 25 per cent indentation in the foam material using an indentor foot smaller than the foam area in accordance with the test on which the specifications of the Rubber Manufacturer's Association (of the United States of America) are based.

In the first embodiment of the cushion 20 illustrated in FIGS. 1-6, the side-to-side width of the cushion is about 18 inches, the front-to-back depth of the cushion is about 15 inches, and the uncompressed thickness of the cushion varies from about 4 inches at the front of the cushion to about 3 inches at the back of the cushion The thickness of the resilient foam material layer 50 is about 1½ inches.

As best illustrated in FIGS. 3 and 4, the additional mass of resilient foam material 56 is disposed on top of the bottom layer 50 in a forward region of the casing 24, and the mass of resilient foam material 56 is adapted to support the seated person's thighs. The forward mass of resilient foam material 56 may be the same open cell, high density, polyurethane foam material as used for the bottom layer of foam material 50. In the embodiment illustrated in FIGS. 3 and 4, the forward mass of foam material 56 is a separate piece of material which is preferably attached with a suitable conventional glue or adhesive to the bottom layer of foam material 50. Alternatively, the forward mass of foam material 56 may be provided as a unitary part of, and extension of, the bottom layer of material 50.

In any event, it is preferred to provide the forward mass of foam material 56 in a unique shape that includes a front portion 58 that is thicker than a sloping rear portion 60. Further, the front portion 58 preferably includes a central portion 62 and lateral portions 64 on either side of the central portion 62. The lateral portions 64 decrease in thickness with increasing distance from the central portion 62. The central portion 62 lies at the front edge of the cushion 20 generally equidistant from each side of the cushion The central portion 62 is thus substantially in registry with the space between the seated person's thighs. Each of the seated person's thighs is substantially in vertical registry with one of the sloping lateral portions 64.

An alternate embodiment of the forward mass of resilient foam material is designated in FIG. 5 generally by the reference numeral 56'. The mass of foam material 56' has a somewhat simpler configuration with a generally uniform thickness front portion 58'. A rear portion 60' tapers from the front portion 58' to a lesser thickness.

The forward mass of foam material 56 or 56' may be provided in other shapes, depending upon the depth of the cushion, the size of the person for which the cushion is designed, the activity, if any, in which the person will be engaged while using the cushion, and other parameters that may be relevant for a specific application.

A fluid-filled pad 70, such as a liquid-filled pad, is positioned on top of a portion of the bottom layer of resilient foam material 50 in the rearward region of the casing 24. The pad 70 extends rearwardly from the forward mass of foam material 56. The pad 70 has a thickness that is substantially equal to the thickness of the rear edge of the forward mass of foam material 56 as best seen in FIG. 4.

In the preferred form of the seat cushion 20 illustrated in FIGS. 1-6, the pad 70 extends rearwardly in a configuration defining a rearwardly opening notch or void over which the seated person's coccyx or sacral area can be positioned. The pad 70 defines lateral portions 71 (FIG. 3) on either lateral side of the void over which the seated person's ischial tuberosities can be positioned.

The fluid-filled pad 70, in the preferred embodiment, contains a liquid or liquid-like substance and comprises a liquid-tight envelope that is fabricated from suitable materials compatible with the liquid or liquid-like substance that is contained within the pad 70. One envelope material that may be used with a variety of liquids is a polyvinylchloride sheet material. The material may be somewhat elastic and can be sealed around the fluid by means of radio frequency welding or vulcanizing. In a preferred form of construction, the pad 70 includes two layers of the polyvinylchloride sheet material to form a double-walled envelope with each layer having a thickness of about 12 mils. A suitable polyvinylchloride sheet material is that provided by WimanCoys, Plastic Division, 11 McCleland Road, St. Cloud, Minnesota 56301, U.S.A. The pad envelope may be filled with the liquid through a conventional duck bill filling valve.

In the preferred form of the cushion illustrated in FIGS. 1-6, the pad 70 preferably includes a liquid or liquid-type material that readily conforms to the contours of the portion of the body impressed onto the cushion 20 over the pad 70. A wide variety of well-known, conventional fluids such as gases, liquids, or liquid-type materials may be used, including those that are sufficiently viscous to have shape-retaining characteristics. As used herein, the term "liquid" in the context of the present invention includes highly viscous liquids such as plastic or thixotropic materials that are flowable under pressure, as well as gels, jellies, and the like.

In one preferred embodiment, the liquid fill material may be a conventional mixture of 1 part by weight methylparaben, 1 part by weight of 18 percent solution sodium hydroxide, 100 parts by weight water, and ½ part by weight polymer, such as that sold in the United States of America under the trade name Carbomer 934P, by B. F. Goodrich, 6100 Oaktree Blvd., Cleveland, Ohio 44131, U.S.A. This is a high molecular weight polymer of acrylic acid cross-linked with a polyalkenyl polyether as taught by U.S. Pat. No. 2,798,053.

In the embodiment of the seat cushion 20 illustrated in FIGS. 1-6, the pad 70 is positioned in the rearward region of the casing 24 and has a width of about 18 inches and a depth of about 7½ inches. The thickness of the pad 70, when all the liquid material within the pad is uniformly distributed, is between about ½ inch and ⅝ inch. The notch or void at the rearward edge of the pad 70 is about 5 inches wide and extends into the pad 70 about 3 inches between the two lateral portions 71. The bottom of the pad 70, or a portion of the bottom of the pad 70, is preferably adhered, with a suitable conventional glue, to the top surface of the resilient bottom layer foam material 50 so as to hold the pad 70 in position.

As best illustrated in FIGS. 3 and 4, the top layer of resilient foam material 80 is disposed to extend over the forward mass of resilient foam material 56 and the pad 70. The foam material 80 also preferably extends over the front of the forward mass of foam material 56 and over the front of the bottom layer of foam material 50.

The top layer of foam material 80 defines a cut-out or void region at the middle of the back edge, and that cut-out or void is in substantial registry with the void defined by the liquid-filled pad 70.

The top layer of foam material 80 is preferably an open cell, low density polyurethane foam material having an indentation load deflection of between about 10 to 20 pounds per 50 square inch area at an indentation of 25 per cent. The thickness of the top layer of resilient foam material 80 preferably ranges from between about ½ inch to about 3 inches. In one preferred embodiment, the thickness is about 1 inch. The foam material 80 may be the type sold in the United States Of America under the trade name Foamex Firestone Soft Urethane Foam as provided by Adams Foam Rubber Company, 4737 South Christiana Ave., Chicago, Illinois 60632, U.S.A.

The first embodiment of the cushion 20 illustrated in FIGS. 1-6 can be used in a variety of ways. However, in a preferred method of supporting a patient, the cushion 20 is initially placed on a suitable base or support surface. The valve 40 is opened so that the resilient contour-conforming means foam material 50 urges the casing 24 toward the expanded condition (FIG. 1). Since the valve 40 is open, air can flow into the interior of the casing 24 as the interior volume of the casing 24 is increased.

When the cushion 20 is provided with the hand inflation valve/pump assembly 46 (FIG. 6), then air may be pumped into the casing 24 to pressurize the casing 24 to ensure sufficient expansion of the cushion 20.

The valve 40 (or 46) may be closed with the cushion in the expanded condition if the person wishes to sit on the expanded cushion. However, it is intended that for most users, the user will open the valve 40 (or 46) immediately prior to the person being properly positioned on the cushion 20. As the person is positioned on the cushion, much of the air will be expelled from the cushion 20 through the valve 40. The interior elements of the cushion will conform to the impressed body configuration. Major portions of the cushion 20 will be substantially compressed. The liquid in the pad 70 will be forced to flow into a conforming configuration.

After it has been ascertained that the person is properly positioned on the cushion 20, the valve 40 (or 46) is then closed. This serves to substantially retain the cushion in the contour-conforming configuration and prevents the cushion from expanding if the person moves on the cushion or is removed from the cushion.

When the person is properly positioned on the cushion 20, the person's buttock region is received in the cushion at a lower elevation than the lower thighs or area of the knees which are supported at a somewhat higher elevation by the thicker forward region of the cushion. The ischial tuberosities are positioned directly over the lateral portion 71 of the liquid-filled pad 70, and the sacral area or coccyx is positioned over the void defined by the pad 70 and by the overlying top layer of foam material 80. The cushion 20 therefore provides a very comfortable seating arrangement. The pressures on the sacral and ischial areas are substantially reduced. The cushion 20 generally holds the shape in conformance with the body seated thereon.

Minor adjustments in seating position can be made on the cushion 20 without creating instability problems and without significantly destroying the support characteristics and contour-conforming characteristics of the cushion.

Further, if desired, the person could be temporarily removed from the cushion, and the cushion could be allowed to expand to its uncompressed configuration by opening the valve 40 (or 46). The person can then be repositioned on the cushion and the valve 40 (or 46) thereafter closed to provide a "new" or "fresh" support.

Thus, it can be seen that a single cushion of the present invention can be used with a variety of body configurations and body weights since the cushion readily conforms to the impressed body contour and can be maintained substantially in that contour. Although it may be desired to provide the cushion in a number of different sizes for, say, large adults, average size adults, small adults, and various sizes of children, an almost custom-like seat cushion effect can be achieved for each person within a selected size range. This has the advantage in institutional use of reducing inventory and simplifying distribution and use of such cushions.

Another embodiment of the present invention is illustrated in FIGS. 7—12 wherein a cushion for supporting the back of a seated human body is designated generally by the reference numeral 120. The cushion includes an airtight casing 124 having a front support layer 126 and a rear bearing layer 136.

Figures 7, 8, 9, 10, 11, 12:
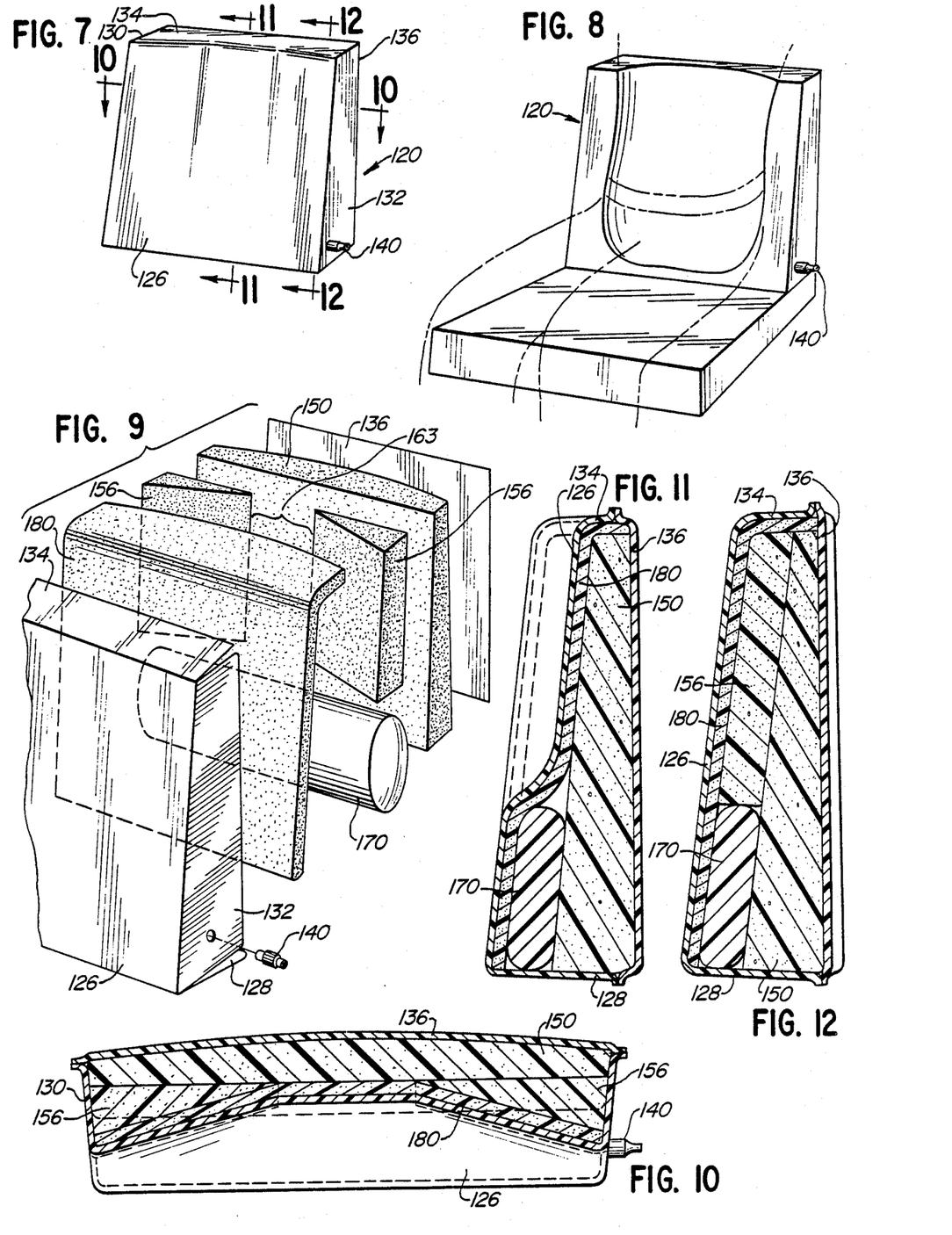
FIG. 7 is a perspective view of another embodiment of the cushion of the present invention shown in use to support the back of a seated person illustrated in phantom by dashed lines.
FIG. 8 is a perspective view showing how the cushion of FIG. 6 conforms to the back of a seated person illustrated in phantom by dashed lines.
FIG. 9 is an enlarged, fragmentary, exploded, perspective view of the cushion shown in FIG. 7.
FIG. 10 is an enlarged, cross-sectional view taken generally along the plane 10—10 in FIG. 7.
FIG. 11 is an enlarged, cross-sectional view taken generally along the plane 11—11 in FIG. 7.
FIG. 12 is an enlarged, cross-sectional view taken generally along the plane 12—12 in FIG. 7.

The front support layer 126 includes a bottom flap 128 (FIGS. 9 and 12), a left side flap 130 (FIG. 10), a right side flap 132 (FIGS. 9 and 10), and a top flap 134 (FIGS. 9 and 12). The top flap 134 is sealed to the left and right side flaps 130 and 132 at the cushion corners at the top. The bottom flap 128 is sealed to the left and right side flaps 130 and 132 at the cushion corners at the bottom. The rear margins of the flaps 128, 130, 132, and 134 are sealed to the periphery of the rear layer 136.

The casing 124 may be fabricated from a variety of conventional materials as described above for the casing 24 of the first embodiment of the cushion 20 illustrated in FIGS. 1-6.

A valve means or valve 140 is mounted to the casing 120 for communicating with the interior of the casing 124. The valve 140 is operable for preventing or permitting flow of air through the valve means into and out of the casing 124 in the same manner as the valve 40 (or 46)

discussed above with respect to the first embodiment of the cushion 20 illustrated in FIGS. 1–6. As with the first embodiment, a hand inflation valve/pump assembly may be provided in the same form as the assembly 46 described above for the first embodiment of the cushion 20.

The back support cushion 120 includes a rear layer of resilient foam material 150 positioned adjacent the casing rear bearing layer 136. The foam material layer 150 extends into an upper region of the casing 124 and into a lower region of the casing 124. The casing lower region is adapted to be disposed adjacent the lower region of the person's back, and the upper region of the cushion 120 is adapted to be disposed adjacent an upper region of the person's back.

The foam material 150 may be the same as the foam material 50 described above with reference to the first embodiment of the cushion 20 illustrated in FIGS. 1–6.

A fluid-filled pad 170 is provided in the lower region of the cushion 120. The pad 170 may be fabricated from the same materials as the pad 70 of the first embodiment of the cushion 20 heretofore described, and, in the one embodiment here described, the pad 170 may contain the same liquid material as the pad 70 or may contain other suitable fluids.

At least one upper mass of resilient foam material 156 is provided in the upper region of the cushion 120 to extend upwardly from the pad 170. Preferably, as illustrated, there are two such masses or pieces of foam material 156. The two masses of foam material 156 are spaced apart so that a central portion 163 of the rear layer of foam material 150 extends between the masses of material 156. Preferably, each upper mass of foam material 156 has a generally wedge shape which is thicker along a lateral, vertical margin of the cushion and which is thinner adjacent the central portion 163 of the rear layer of resilient foam material 150.

Each upper mass of resilient foam material 156 may be fabricated from the same material as used for the rear layer of foam material 150. In the embodiment illustrated, each upper mass of resilient foam material 156 is a separate piece that may be adhered, by glue or other suitable adhesive, to the rear layer of foam material 150. However, the upper masses of resilient foam material 156 may be formed as a unitary extension of the rear layer of foam material 150.

Finally, a front layer of resilient foam material 180 is disposed to extend over the upper masses of resilient foam material 156, over the central portion 163 of the rear layer of resilient foam material 150, and over the pad 170. The upper end of the front layer of resilient foam material 180 extends over the top end of each of the upper masses of foam material 156 and over the top end of the rear layer of foam material 150.

The front layer of foam material 180 may be the same material as the top layer of foam material 80 used in the first embodiment of the cushion 20 described above with reference to FIGS. 1–6. In particular, it is preferred that the front layer of foam material 180 be softer (have less resistance to compressive forces) than the foam materials 156 and 150.

The foam materials 180, 156, and 150 may be adhered together with suitable conventional glues or adhesives.

The back support cushion 120 may be used in a manner analogous to the use of the seat support cushion 20 described above with reference to FIGS. 1–6. In particular, the valve 140 is initially opened before the person leans against the cushion 120. This permits the cushion 120 to be urged by the resilient foam materials to the expanded condition. Next, the person's back is positioned against the cushion 120, and the air is expelled from the cushion through the open valve 140. Finally, after the person's back is properly positioned, the valve 140 is closed so as to maintain the conformity of the cushion 120 with the person's back.

The internal components of the cushion 120 can be altered in number, size, and shape to accommodate various anatomical requirements or to permit the cushion to be adapted for a specialized support function.

For example, the cushion 120, as well as the first embodiment of the cushion 20, may be adapted for use in supporting a specific extremity or other portion of the human body. The cushion may be adapted for use as part of a splint assembly for cushioning or immobilizing a portion of a body.

In light of the teachings of the present invention, it will be appreciated that in some applications involving some specific design features of the cushion, the foam materials should remain substantially unbonded to the flexible, airtight casing in accordance with the teachings of one aspect of the invention. However, with other specific design features in other applications, the cushion materials may be bonded in places to the casing in accordance with the teachings of another aspect of the invention.

It will be realized that modifications may be made to the invention described herein without departing from the essential spirit and scope. The following claims are intended to encompass all such modifications.

What is claimed is:

1. A support cushion for a seated human body comprising:
   a flexible, airtight casing having at least a top support layer and a bottom bearing layer, said casing having a forward region to be disposed under the body's thighs and a rearward region to be disposed under the body's buttocks;
   valve means mounted to said casing for communicating with the interior of said casing and operable for preventing or permitting flow of air through said valve means into and out of said casing;
   a bottom layer of resilient foam material positioned on said casing bottom bearing layer and extending into said forward and rearward regions of said casing;
   a fluid-filled pad positioned on top of a portion of said bottom layer of resilient foam material in said rearward region of said casing, said pad extending rearwardly from said forward region in a configuration defining a void over which the seated body's sacral area and coccyx can be disposed and defining lateral portions on bolt lateral sides of said void over which the seated body's ischial tuberosity area can be disposed;
   a forward mass of resilient foam material extending forwardly of said pad in said casing forward region over which the seated body's thighs can be disposed; and
   a top layer of resilient foam material disposed to extend over said forward mass of resilient foam material and said pad, said top layer of resilient foam material extending into said rearward region of said casing in a configuration defining a top layer void defining top layer lateral portions on both sides of said top layer void, said top layer lateral portions being generally in registry with said pad lateral portions to generally register said top layer void with said pad void.

2. The cushion in accordance with claim 1 in which said cushion is thicker in said forward region of said casing than in said rearward region of casing.

3. The cushion in accordance with claim 2 in which said casing top support layer slopes generally downwardly from said forward region to said rearward region.

4. The cushion in accordance with claim 1 in which said forward mass of resilient foam material is separate from said bottom layer of resilient foam material.

5. The cushion in accordance with claim 4 in which said forward mass of resilient foam material is glued to said bottom layer of resilient foam material.

6. The cushion in accordance with claim 1 in which said bottom layer of resilient foam material is an open cell polyurethane foam material having a indentation load deflection from between about 35 and about 45 pounds per 50 square inch area at 25 per cent indentation.

7. The cushion in accordance with claim 1 in which said forward mass of resilient foam material is an open cell polyurethane foam material having an indentation load deflection of between about 35 and about 45 pounds per 50 square inch area at 25 per cent indentation.

8. The cushion in accordance with claim 1 in which said top layer of resilient foam material is an open cell polyurethane foam material having an indentation load deflection of between about 10 and about 20 pounds per 50 square inch area at an indentation of 25 per cent.

9. The cushion in accordance with claim 1 in which said top layer of resilient foam material is glued to said forward mass of resilient foam material.

10. The cushion in accordance with claim 1 in which said fluid-filled pad comprises a liquid-tight envelope that is fabricated from polyvinylchloride sheet material and that is filled with a liquid.

11. The cushion in accordance with claim 10 in which said envelope is double-walled and includes two layers of said polyvinylchloride sheet material which each have a thickness of about 12 mils.

12. The cushion in accordance with claim 10 in which said liquid is sufficiently viscous to have shape-retaining characteristics.

13. The cushion in accordance with claim 12 in which said liquid includes a mixture of a polymer, water, sodium hydroxide, and methylparaben.

14. The cushion in accordance with claim 1 in which said forward mass of resilient foam material includes a front portion that is thicker than said fluid-filled pad and that includes a rear portion tapering from said front portion to a lesser thickness that is substantially equal to the thickness of said fluid-filled pad.

15. The cushion in accordance with claim 1 in which said forward mass of resilient foam material includes a central portion and includes lateral portions extending from said central portion, said lateral portions decreasing in thickness with increasing distance from said central portion.

16. The cushion in accordance with claim 1 in which said forward mass of resilient foam material is unitary with said bottom layer of resilient foam material.

17. The cushion in accordance with claim 1 in which said bottom layer of resilient foam material has a lower surface which is convex downwardly so as to generally conform with the curvature of a conventional wheelchair sling seat.

18. A support cushion for a seated human body comprising:
   a flexible casing having at least a top support layer and a bottom bearing layer, said casing having a forward region to be disposed under the body's thighs and a rearward region to be disposed under the body's buttocks;
   a bottom layer of resilient foam material positioned on said casing bottom bearing layer and extending into said forward and rearward regions of said casing;
   a fluid-filled pad positioned on top of a portion of said bottom layer of resilient foam material in said rearward region of said casing, said pad extending rearwardly from said forward region in a configuration defining a void over which the seated body's sacral area and coccyx can be disposed and defining lateral portions on both lateral sides of said void over which the seated body's ischial tuberosity area can be disposed;
   a forward mass of resilient foam material extending forwardly of said fluid-filled pad in said casing forward region over which the seated body's thighs can be disposed, said forward mass of resilient foam material including a front portion that is thicker than said fluid-filled pad and that extends to an elevation higher than the upper surface of said fluid-filled pad, said forward mass of resilient foam material including a rear portion having an upper surface tapering from said front portion to substantially the same elevation as the top of said fluid-filled pad, said front and rear portions of said forward mass of resilient foam material having a combined length extending forwardly from said fluid-filled pad for supporting the seated body's thighs forwardly of the body's buttocks, said forward region of said cushion below said forward mass of resilient material being devoid of any fluid-filled pad below said forward mass of resilient foam material; and
   a top layer of resilient foam material disposed to extend over said forward mass of resilient foam material and said fluid-filled pad, said top layer of resilient foam material being of substantially uniform thickness where it overlies said fluid-filled pad and said forward mass of resilient material, said top layer of resilient foam material conforming to the tapered upper surface of said forward mass of resilient material, said top layer of resilient foam material extending into said rearward region of said casing in a configuration defining a top layer void and defining top layer lateral portions on booth sides of said top layer void, said top layer lateral portions being generally in registry with said pad lateral portions to generally register said top layer void with said pad void.

19. The cushion in accordance with claim 18 in which said cushion is thicker in said forward region of said casing than in said rearward region of said casing.

20. The cushion in accordance with claim 19 in which said casing top support layer slopes generally downwardly from said forward region to said rearward region.

21. The cushion in accordance with claim 18 in which said forward mass of resilient foam material is separate from said bottom layer of resilient foam material.

22. The cushion in accordance with claim 21 in which said forward mass of resilient foam material is glued to said bottom layer of resilient foam material.

23. The cushion in accordance with claim 18 in which said forward mass of resilient foam material is separate from said top layer of resilient foam material.

24. The cushion in accordance with claim 18 in which said top layer of resilient foam material is an open cell polyurethane foam material having an indentation load deflection of between about 10 and about 20 pounds per 50 square inch area at an indentation of 25 per cent.

25. The cushion in accordance with claim 18 in which said top layer of resilient foam material is glued to said forward mass of resilient foam material.

26. The cushion in accordance with claim 18 in which said fluid-filled pad comprises a liquid-tight envelope that is fabricated from polyvinylchloride sheet material and that is filled with a liquid.

27. The cushion in accordance with claim 26 in which said envelope is double-walled and includes two layers of said polyvinylchloride sheet material which each have a thickness of about 12 mils.

28. The cushion in accordance with claim 26 in which said liquid is sufficiently viscous to have shape-retaining characteristics.

29. The cushion in accordance with claim 28 in which said liquid includes a mixture of a polymer, water, sodium hydroxide, and methylparaben.

30. The cushion in accordance with claim 18 in which said forward mass of resilient foam material includes a central portion and includes lateral portions extending from said central portion, said lateral portions decreasing in thickness with increasing distance from said central portion.

31. The cushion in accordance with claim 18 in which said forward mass of resilient foam material is unitary with said bottom layer of resilient foam material.

32. The cushion in accordance with claim 18 in which said bottom layer of resilient foam material has a lower surface which is convex downwardly so as to generally conform with the curvature of a conventional wheelchair sling seat.

33. The cushion in accordance with claim 18 in which said casing is airtight; and
 a valve means mounted to said casing for communicating with the interior of said casing and operable for preventing or permitting flow of air through said valve means into and out of said casing.

* * * * *